United States Patent
Mani

[19]

[11] Patent Number: 6,110,342
[45] Date of Patent: Aug. 29, 2000

[54] PROCESS FOR PRODUCTION OF AMINO ACID HYDROCHLORIDE AND CAUSTIC VIA ELECTRODIALYSIS WATER SPLITTING

[75] Inventor: K. N. Mani, Basking Ridge, N.J.

[73] Assignee: Archer Daniels Midland Company, Decatur, Ill.

[21] Appl. No.: 09/223,054

[22] Filed: Dec. 30, 1998

Related U.S. Application Data

[63] Continuation-in-part of application No. 09/193,626, Nov. 11, 1998.
[60] Provisional application No. 60/093,558, Jul. 21, 1998.
[51] Int. Cl.[7] .................................................. B01D 61/44
[52] U.S. Cl. .......................... 204/527; 204/530; 204/531; 204/534; 204/537; 204/538; 204/540; 204/541
[58] Field of Search ...................... 204/527, 530, 204/531, 534, 537, 538, 540, 541

[56] References Cited

U.S. PATENT DOCUMENTS 5,049,250  9/1991  Chlanda ................................. 204/534

*Primary Examiner*—Arun S. Phasge
*Attorney, Agent, or Firm*—Laff, Whitesel & Saret, Ltd.; J. Warren Whitesel

[57] ABSTRACT

The invention uses a stack of three compartment electrodialysis cells in a process for the production amino acid hydrochloride and an alkali. The electrodialysis cell contains bipolar, cation and anion membranes which are arranged to form acid, base and salt compartments. The process begins with supplying a salt solution to the salt compartment, water to the base compartment, and a liquid comprising an amino acid to the acid compartment. Preferably, the feed salt is sodium chloride or potassium chloride or lithium chloride. A direct current driving force is applied across the cell to convert the salt solution to an alkali in the base compartments and an amino acid hydrochloride in the acid compartment. The acid and alkali solutions and a depleted salt solution are withdrawn from their respective compartments. A chelating agent may be added to the salt solution before it is fed into the electrodialysis cell.

15 Claims, 7 Drawing Sheets

PROCESS FOR PRODUCTION OF AMINO ACID HYDROCHLORIDE AND CAUSTIC VIA ELECTRODIALYSIS WATER SPLITTING

This application is a formal application replacing my pending provisional application Ser. No.: 60/093,558, filed Jul. 21, 1998, and also is a continuation-in-part of my prior application Ser. No. 09/193,626, filed Nov. 11, 1998, pending, which in turn was also a formal application replacing my provisional application Ser. No. 60/093,558, filed Jul. 21, 1998.

This invention relates to a co-production, via an electrodialysis water splitting, of hydrochlorides of amino acids and caustic soda using salt and an appropriate amino acid as the starting raw materials.

FIELD OF THE INVENTION

The invention is based on a discovery that (a) an amino hydrochloride salt formed in an acid product loop of an electrodialysis cell is satisfactorily contained within the loop. This containment enables the production of a caustic co-product with a purity sufficient for commercial use or sale. The excellent containment of the amino acid component(s) within the acid loop also means that the amino acid feed solution need not be subject to costly purification steps, even though the feed solution may contain impurities such as calcium and magnesium. (b) The in-situ production of hydrochloride substantially reduces the chloride transport across a bipolar membrane, thereby producing a coustic having quality which is higher than the quality of caustic which is obtained by the simple conversion of salt to caustic soda and hydrochloric acid. (c) The production of the hydrochloride results in a higher process efficiency and lower overall production costs. (d) A high concentration of hydrochloride can be produced and processed efficiently.

The inventive process is carried out in a three compartment electrodialysis cell ("ED") having bipolar, cation and anion exchange membranes. A bipolar membrane is a membrane which splits water and prevents the passage of both anions and cations. Usually, the salt feed stream into the cell is obtained as a near saturated solution by dissolving rock salt (or a similar salt source) in fresh water and/or by a use of a depleted salt solution derived from the cell. The concentrated salt solution is then purified via a pH adjustment/filtration and optionally with polishing ion exchange. The purified solution is fed to the salt loop of the cell.

The addition of small amounts of a chelating/sequestering agent, such as ethylenediamine tetra-acetic acid (EDTA), to the salt loop is effective in improving the process reliability by providing a chelating action with residual multivalent cation impurities (especially calcium), thereby mitigating the fouling of cation membranes. This chelating action is aided by the fact that the high selectivity/efficiency for the production of the hydrochloride causes the salt loop to remain basic (pH>7), thereby enhancing the stability and solubility of the chelate complexes (with the multivalent cationic impurities). Thus, the complexes are retained within the salt loop. As a result, a polishing ion exchange step for the salt feed is not usually essential.

The inventive process may be used in the production of a variety of amino acid hydrochlorides and the co-production of a high quality caustic. The process is particularly useful in the production of hydrochloride wherein the associated amino acid is basic (arginine, lysine, hydroxlysine, histidine) or contains three or more carbon atoms. The inventive process is particularly useful in the production of lysine hydrochloride. Depending on the salt being processed (NaCl or KCl or LiCl), the co-product base is caustic soda (NaOH) or caustic potash (KOH) or Lithium Hydroxide.

Amino acids are produced in commercial quantities by either fermentation of sugars or chemical synthesis. Many of these products are isolated or sold in the form their hydrochloride salt. Lysine hydrochloride is one such example. It is produced by reacting a purified lysine base with concentrated hydrochloric acid. The acid is typically purchased from byproduct sources or from chlor-alkali manufacturers who produce it by reacting chlorine with hydrogen and then dissolving the resulting hydrogen chloride gas in water to obtain the concentrated acid. The cost of the purchased acid is often significant. One also has to deal with the supply, delivery and safety problems which are associated with the handling of the acid.

Bipolar membrane based electrodialysis (ED) is another alternative means for directly generating caustic and hydrochloric acid from salt. The bipolar membrane splits water and prevents the passage of both anions and cations.

FIG. 1 shows a three compartment cell used in the practice of the inventive process. The cell comprises bipolar 46 membrane (indicated by the symbol (−+)), anion membrane (−) 50, and cation membrane (+) 48 arranged in alternating layers. The three compartments of the electrodialysis cell are located between the membranes and are designated acid (A), base (B) and salt (S). The entire combination of membranes and compartments is termed a "unit cell" or, simply, a "cell". Many (perhaps 100–200) such cells may be assembled between a single set of electrodes (an anode, + and a cathode, −) to form a compact "electrodialysis stack."

The feed stream salt solution is fed to the salt compartment S which is located between cation and anion membranes. A liquid comprising water is fed to the acid and base compartments A and B located on either side of the bipolar membrane 46, as shown in FIG. 1.

Under a direct current driving force the H$^+$ and OH$^-$ ions generated at the bipolar membrane are transported to the acid and base compartments A and B, respectively. Concurrently the Cl$^-$ and Na$^+$ ions produced by the dissociation of salt (NaCl) are transported across the anion and cation membranes 50, 48, respectively. In the base compartment B, the Na$^+$ ions combine with the OH$^-$ ions to form the base product. In a similar manner the Cl$^-$ ions combine with the H$^+$ ions in the acid compartment A to form the acid product. The net effect is the production of relatively pure acid (HCl) and base (NaOH) products from the salt (NaCl).

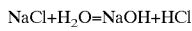

In terms of both capital and energy costs, the ED process is less expensive than a chlor-alkali process. However, the ED process can generate only a dilute hydrochloric acid (2–7 wt %) and caustic soda (5–18 wt %) products. In order to use the acid in the production of hydrochloride, one would have to concentrate the acid at an additional cost.

Furthermore, since a bipolar membrane is not perfectly perm-selective, small amounts of Cl$^-$ and Na$^+$ ions may be transported across the bipolar membrane, resulting in product contamination. That is, the caustic product may contain some chloride ions and the acid product may contain sodium ions. In the production of dilute acid and base from salt, a caustic co-product has 1–4 mole % chloride, while the acid product has 2–5.5 mole % sodium contaminant present. (K. N. Mani, "Electrodialysis Water Splitting Technology", J.

Membrane Sci., (1991), 58, 117–138). Such levels of contamination can pose problems in terms of a reagent (i.e., NaCl) loss, as well as reducing the values of the product acid and base.

Methods for improving the caustic and/or acid purity may involve the use of multichamber cells having two or more bipolar membranes as outlined in U.S. Pat. Nos. 4,976,838; 5,135,626; 5,162,076; 5,198,086; and 5,200,046. However, these patents involve cell designs that are more complicated and expensive than a three compartment cell.

It should be pointed out that in the production of the amino acid hydrochloride by the process of reacting the amino acid with concentrated HCl, the presence of certain amounts of sodium contaminant is not a major problem, since the hydrochloride product is usually recovered by crystallization from a solution. However, contamination of the caustic with the chloride would raise an economic issue.

A novel process is needed for enabling a direct production of the amine hydrochloride using salt and the amino acid as the raw materials. It is important that the co-product caustic be of good and marketable quality.

SUMMARY OF THE INVENTION

In keeping with the aspect of the invention, a process for production amino acid hydrochloride and an alkali is carried out in a three compartment electrodialysis cell containing bipolar, cation and anion membranes. The membranes form acid, base and salt compartments.

The process begins with a salt dissolution step by supplying a salt solution feed stream to the salt compartment, a liquid comprising water to the base compartment, and a liquid comprising an amino acid to the acid compartment. Preferably, the feed stream is either sodium chloride or potassium chloride. Then, a direct current driving force is applied to effect a conversion of the salt to an alkali in the base compartment and the amino acid hydrochloride in the acid compartment. Next, the acid and alkali products as well as the depleted salt solutions are withdrawn from their respective compartments.

Preferably, the feed salt stream is purified before its entry into the salt compartment in order to remove multivalent contaminants to a suitably low level. Also, a chelating agent may be added to the salt solution feed stream prior to feeding it to the electrodialysis cell. The production of the amino acid hydrochloride in this manner substantially reduces the chloride contamination of the caustic co-product (i.e., a purer caustic co-product).

BRIEF DESCRIPTION OF THE DRAWINGS

The invention and preferred embodiments thereof will become more apparent from a reading of the following specification in connection with the following drawings, in which.

DETAILED DESCRIPTION OF THE INVENTIVE PROCESS

I have found that, in a bipolar membrane based ED process, the hydrochloride can be generated within the acid loop by directly reacting the amino acid with the hydrochloric acid generated therein, thereby avoiding the hazards and cost of handling the concentrated hydrochloric acid. The reaction, which occurs within the acid loop of the cell, permits the amino acid to be reacted with the concentrated (30–35 wt %) HCl that is generated therein. There is no product dilution penalty such as that which occurs in the prior art. Consequently, the quality of the amino acid hydrochloride produced by the inventive process is essentially equivalent to that produced by the current process using an external reaction employing purchased (concentrated) acid.

The concept of an in situ product conversion is mentioned in the above-cited paper by K. N. Mani. One example of this conversion is the neutralization of caustic generated in a bipolar ED cell with sodium bisulfite to form the sulfite in the SOXAL® process. (U.S. Pat. Nos. 4,082,835; 4,107,015; and 5,281,317).

However, the inventive process for amino acid hydrochloride production is unique and novel in light of the following:

The production, handling and transport of a hazardous chemical (i.e., concentrated HCl) is avoided, while the product quality and strength are not compromised.

The hydrochloride is contained within the acid loop at a surprisingly high level of effectiveness. As a result, the co-product caustic soda is "water white" with no detectable amino acid (lysine being the major amino acid used in my experiments) present in it. Therefore, the quality of the caustic is excellent. Concurrently, the salt loop was also found to remain water white and to have no detectable level of lysine. These facts were demonstrated and confirmed by a long term test (>1200 hours) in the production of lysine HCl in a pilot ED cell.

It is thought that the excellent containment of the hydrochloride is also useful for the production of most amino acids. This result is due in part to the large size of the amino acid molecule (i.e., permitting size exclusion by the ion exchange membranes). It is also due to the unique ability of the amino acid to be in the appropriate ionic form in the vicinity of the bounding membranes of the acid loop. (Please see Diaion® Manual of Ion Exchange Resin and Synthetic Adsorbent Volume II, page 118, Mitsubishi Kasei Corporation, (1992)). The ionic form inhibits the transport of the amino acid out of the acid loop, namely: the ions are acidic in the vicinity of the cationic bipolar membrane surface, and neutral (or even alkaline) in the vicinity of the anion membrane surface.

At the cation surface of the bipolar membrane:

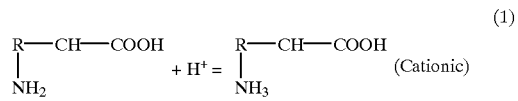

(1)

At the surface of the anion membrane

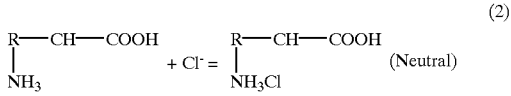
(2)

Figure 1:
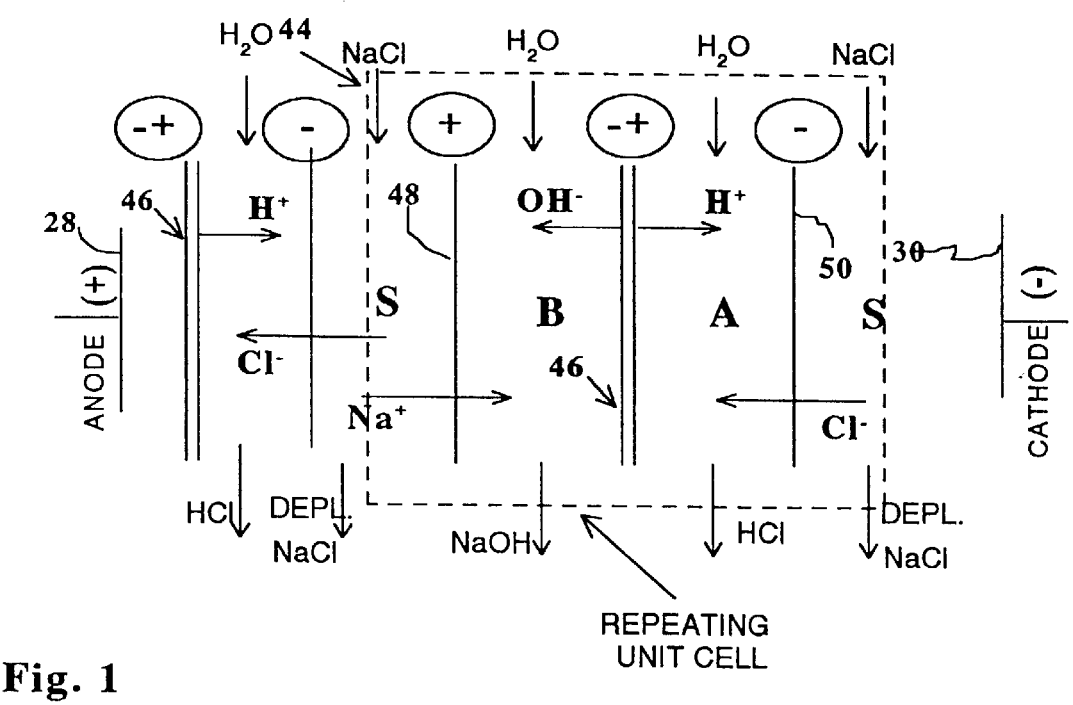
FIG. 1 schematically shows a three compartment cell for using the inventive process.
Figure 2:
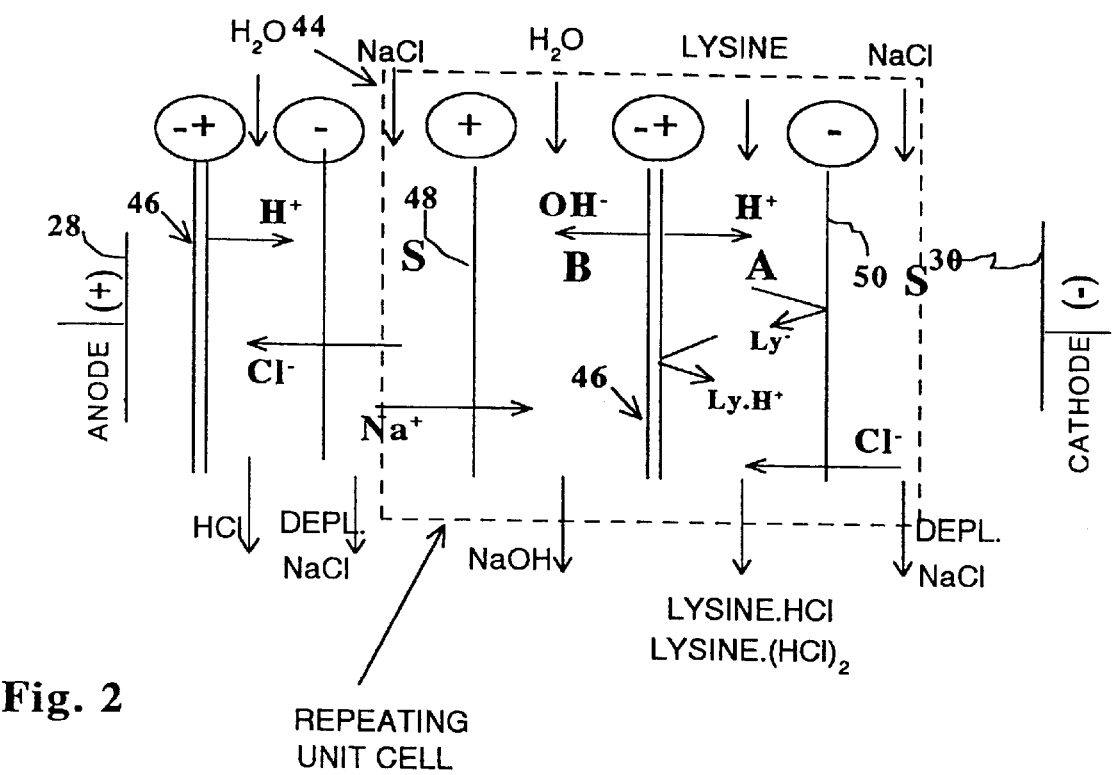
FIG. 2 schematically indicates how the inventive process is carried out in the cell of FIG. 1.

The process is shown schematically in FIG. 2, using lysine (indicate as "Ly") as the feed stream amino acid. In the acid loop (A), the lysine feed reacts with the protons ($H^+$) generated by the bipolar membrane and the chloride ions transported across the anion membrane, yielding lysine hydrochloride (lysine HCl).

Lysine has two amine sites; therefore, in the vicinity of the bipolar membrane, it can combine with a second HCl molecule in order to yield the di-hydrochloride (lysine.$(HCl)_2$). Either species (lysine . HCl or Lysine . $(HCl)_2$) will exist in the protonated form of lysine.$H^+$ (indicated in FIG. 2 as ly.$H^+$). This positively charged ion is readily transported away from the bipolar membrane by the applied electrical field. As shown in equation (2) above near the anion membrane reaction with the chloride ion results in the formation of a neutral specie, which is once again excluded by the ion exchange membranes.

Consequently, the transport of the hydrochloride is inhibited across both the bipolar 46 and anion 50 membranes, leading to the non-detectable levels of amino acid in the base and salt loops, as mentioned earlier. It is possible that, due to diffusion considerations, any amino acid molecules that are quite small (e.g., glycine) could be transported in small amounts across the ion exchange membranes. Nevertheless, the direct reaction process for hydrochloride production is expected to be valid for larger amino acids containing 3 more (preferably 4 or more) carbon atoms.

The process is particularly applicable for basic amino acids, namely: arginine, lysine, hydroxlysine and histidine. These amino acids have a large size (6 carbon atoms per molecule) and do not diffuse readily across the ion exchange membranes. Preferably, the molecules have at least four carbon atoms per molecule. Their high isoelectric points provide better buffering with the chloride ions. The isoelectric points PI is the pH at which the amino acid's dissociation to cations and anions is equal. For basic amino acids, the high pI is the result of an excess of amine groups over the carboxyl groups.

When amino acid hydrochloride is produced, the chloride contamination of the co-product caustic soda is found to be substantially less than the contamination associated with hydrochloric acid production. This surprising result is believed to result from the strong binding of the amino acid with the HCl within the acid compartment. This binding, in turn, effectively reduces the free chloride available for transport across the bipolar membrane 46. In any event, the caustic product of this invention is cleaner than the caustic of prior art processes and, hence, is more valuable.

The overall process efficiency for the practice of this invention was found to be significantly higher than the efficiency with hydrochloric acid production. Efficiency is determined by the equivalents of caustic/amino acid hydrochloride produced per faraday (96500 coulombs) of current input. This higher efficiency, in turn, results in lower energy (electric power) and capital (membrane requirements) cost per unit of product.

A preferred salt feed is sodium chloride, or potassium chloride. More generally speaking, an alkali metal chloride such as sodium chloride, potassium chloride a lithium chloride may be used. Depending upon which of these alkali metal chlorides is used, the caustic co-product is sodium hydroxide, potassium hydroxide, or lithium hydroxide.

Due to the high selectivity of the anion membrane in this inventive process, the salt loop actually tends to become basic (pH ~8–14). In this case, the salt solution feed stream will have a certain amount of $OH^-$ ions, which would also be transported to the acid loop. This process inefficiency has been found to be quite small. The reaction of the transported hydroxide with the amino acid in the acid loop is, as follows:

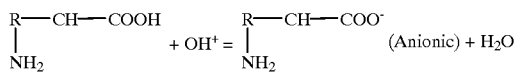
(3)

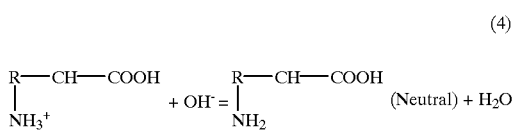
(4)

When the salt loop is basic, the anion membrane which bounds it is also basic, particularly at the surface of the membrane in contact with the salt loop. It is thought that this factor further assists the retention of the amino acid hydrochloride within the acid loop via step (3) above. In U.S. Pat. No. 5,049,250, Chlanda has offered a similar rationale to explain the efficient separation of amino acids from the associated salt contaminants.

For a successful operation of the process of this invention, two operational parameters need to be met on a long term basis. They are:

1. The ion exchange membranes should be free of defects (pinholes, cracks, etc.). The membranes should have long term durability and should not be fouled by contaminants in the streams, such as multivalent cations (calcium, magnesium etc.) and organics (such as from the amino acid feed stream). If necessary, the contaminants need to be removed via suitable pre-treatment.
2. The ED cell hardware (i.e., gasket, end plates, etc., used to form the various compartments and to position the membranes) should remain free of internal leaks during extended periods of operation. In principle, many of the commercially available cell designs may be used. A particularly suitable design is outlined in my pending application Ser. No. 08/784,050 and was used in demonstrating the process of this invention.

Figure 3:
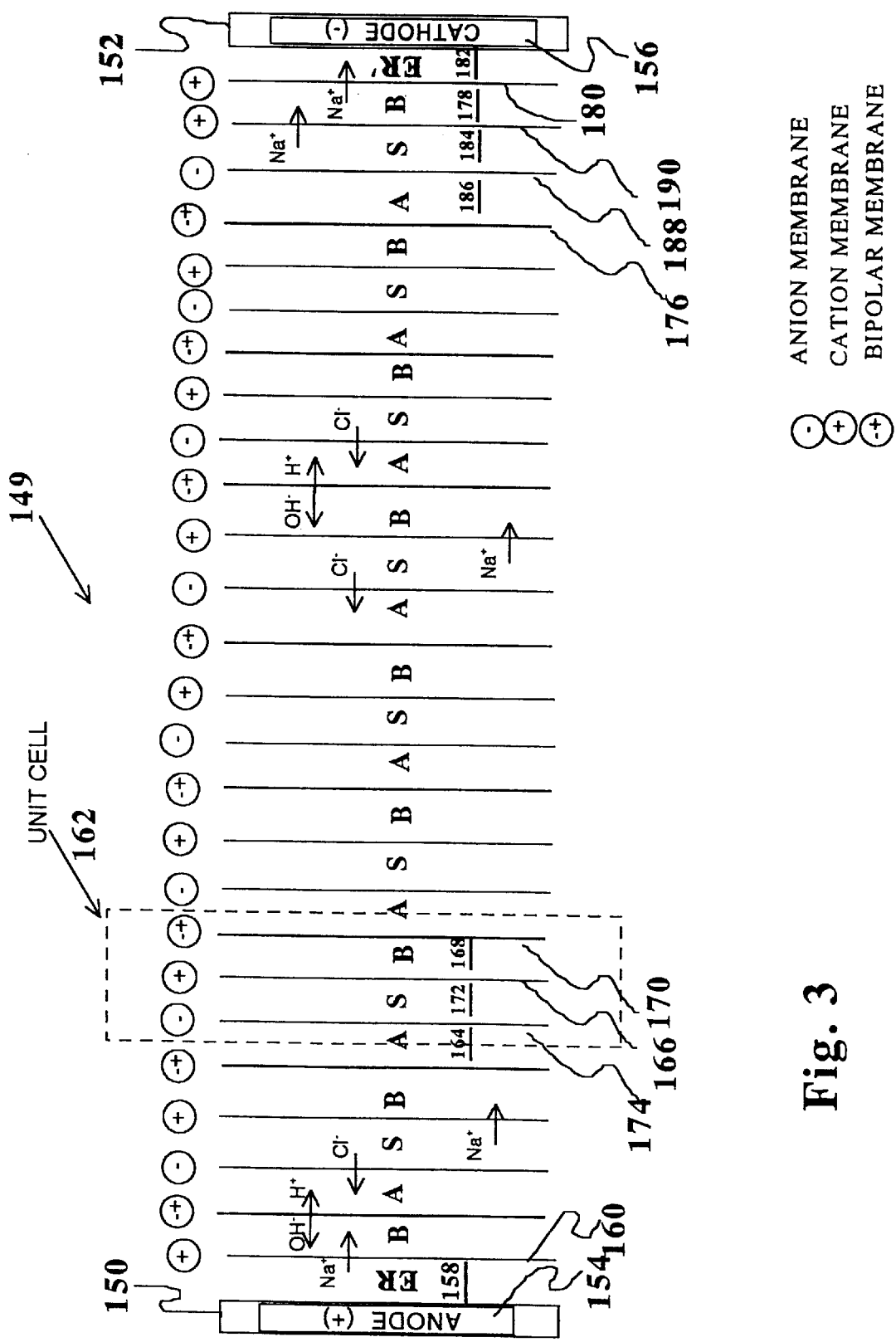
FIG. 3 schematically shows an eight cell pilot electrodialysis stack used during experiments described hereinafter, the stack being assembled in the three compartment configuration of FIGS. 1 and 2.

The novel process of this invention can be better understood from the following examples. All experiments were carried out using an eight cell pilot electrodialysis stack that was assembled in the three compartment configuration, as shown in FIG. 3.

The stack 149 includes end plates 150 and 152 to which the electrodes 154, 156 are attached and through which solutions were fed to and removed from the stack. Gaskets, 1 mm thick, separate the membranes and form the solution compartments. Each gasket had an open central area of 465 $cm^2$ (0.5 $ft^2$), through which the electrical current could pass. The open central areas are filled with a non-woven meshed screen that keep the membranes separated and well supported. The non-woven mesh screen also promotes good flow turbulence. Holes punched in the gaskets are aligned to form internal manifolds. Slots (ports) connecting the manifold with the open central area provide a flow of solution into and out of each compartment.

The stack employed a nickel anode 154, an electrode rinse compartment ER 158, CMT, SPS or Nafion 324® cation membrane 160 and eight repeating cells. The CMT membrane was from Asahi Glass, SPS membrane was from Aqualytics Inc. and the Nafion membrane from DuPont. Each of the eight cells (for example 162) includes an acid compartment A 164, an AHA-2 or AAV anion membrane 174 (the AHA-2 from Tokuyama Corporation, the AAV from Asahi Glass), a salt compartment S 172, an SPS cation membrane 166, a base compartment B 168 and an AQ or BP1 bipolar membrane 170. The AQ membrane was from Aqualytics and the BP1 from Tokuyama Corporation. Of the eight bipolar membranes in the stack 162, the last membrane 176 was followed by an acid compartment A 186, an AHA-2 or AAV anion membrane 188, a salt compartment S 184, an SPS cation membrane 190, a base compartment B 178, a second CMT or SPS cation membrane 180, an electrode rinse compartment ER' 182, and a stainless steel cathode 156.

Figure 4:
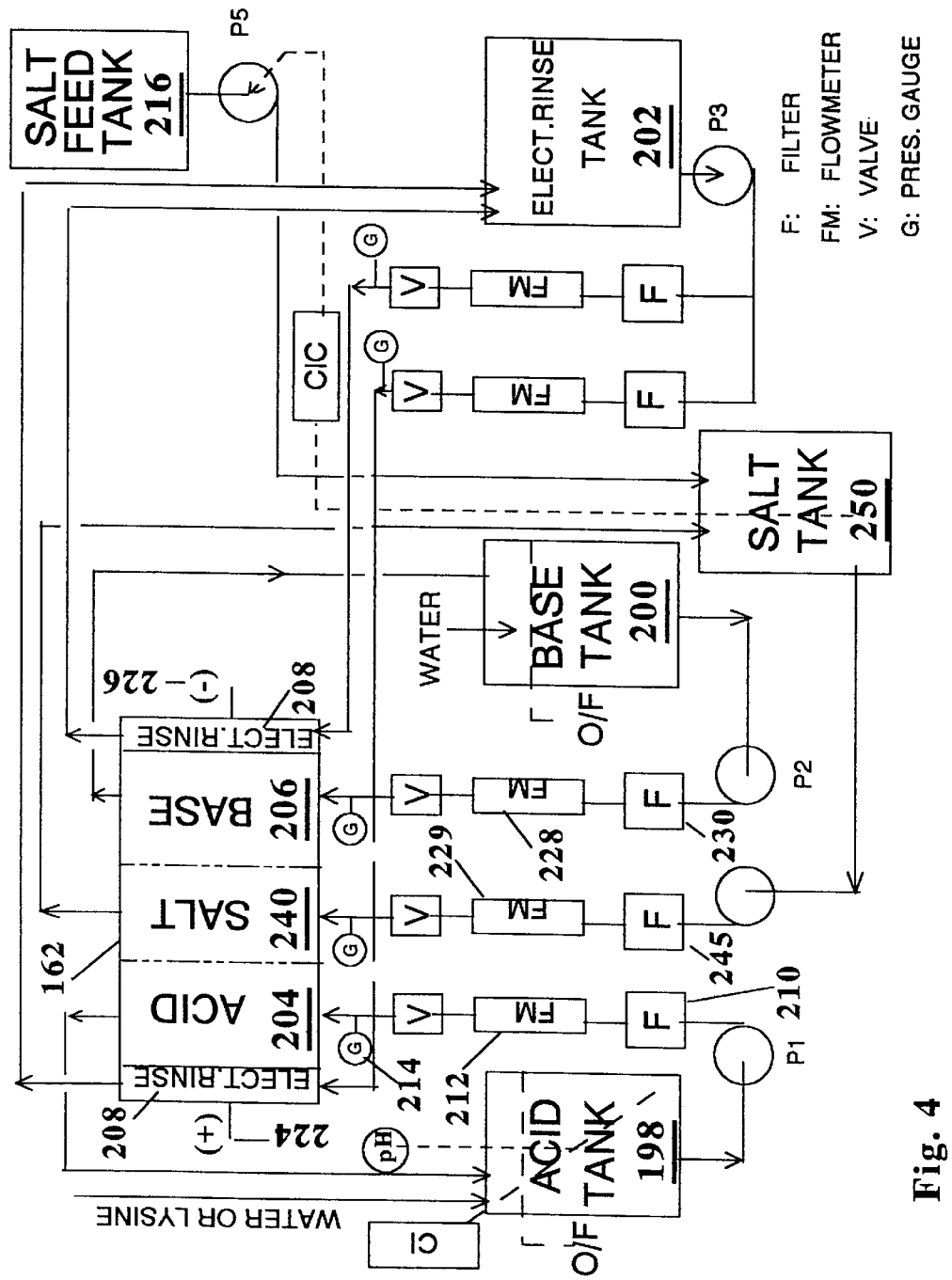
FIG. 4 is a block diagram which shows a system for carrying out the inventive process.

The assembled stack 149 was placed in the system as schematically shown in FIG. 4 in order to carry out the electrodialysis experiments. Four pumps (P1–P4) were used to circulate solutions at the rate of 2.5–4 l/min. from their respective recycle tanks 198, 250, 200, 202 to the acid (204), salt (240), base (206), and electrode rinse compartments (208). Each of the recycle tanks had a nominal volume of 5 liters. The acid, base, and salt loops were operated in a feed and bleed mode.

During operation, a concentrated salt solution that had been filtered and otherwise pre-treated to reduce multivalent contaminants to a very low level was added (via a pump P5) from a salt feed tank 216 using a conductivity controller CIC. The feed tank 216 had the capacity to hold as much as 186 liters of the feed salt solution. During operation, 80–85% of the salt feed to 250 was converted to acid and base. The remainder of the salt solution overflowed from the salt tank 250 and was discarded. Dilution (de-ionized) water was added to the base recycle tank 200 via a metering pump (not shown). The product caustic soda overflowed. In a similar fashion, water or lysine feed (100–500 gm/l concentration) was added to the acid tank 198 via metering pump (not shown). The acid product overflowed. A conductivity indicator Cl and pH meter (pH) helped monitor the operation of the acid loop.

Cartridge filters F 210, flow meters FM 212, and pressure gauges G 214 were used in each loop to ensure a flow of clear fluids at known flow rates and pressure drops in the various recycle loops. A DC power supply (not shown) was connected to the anode and cathode terminals 224, 226 of the stack. The requisite controllers for providing and controlling the electrical input and voltage are located in the power supply itself.

The process can run uninterrupted on a round the clock basis, by ensuring that adequate amounts of pre-treated salt solution, de-ionized water, and/or lysine feeds were available and supplied as needed. Preferably, the pre-treatments reduce multivalent contaminants in the salt feed to a low level. The electrode rinse tank was initially charged with ~10 wt % sodium hydroxide. During operation, the only requirements were a periodic make up of water to compensate for the loss to hydrogen, oxygen generation and evaporation and to insure (via titration) that there was an adequate concentration of caustic.

A feed salt solution was prepared by dissolving 98+% purity NaCl, either supplied by G. S. Robbins or commercially purchased rock salt in water. Sodium carbonate, sodium hydroxide and optionally a phosphate, oxalate and/or granular carbon, were added. The addition of sodium hydroxide/carbonate elevated the pH of the salt solution to 9–10.5 and helped precipitate calcium/magnesium values. The solution was passed through a cartridge filter ($5\mu$ rating) and then subjected to nanofiltration using DK-5 elements (obtained from Desal Osmonics) having a nominal molecular weight cut off of ~200 Daltons. These elements are known to have a substantial rejection for multivalent cations. In actual trials, the nano-filtration step yielded a clear salt solution which had no detectable magnesium, but which contained 0–15 ppm calcium.

In the electrodialysis process, 80–85% of the sodium chloride in the feed was converted to caustic and hydrochloric acid in the base and acid loops respectively. A certain amount of water is also transported to the acid and base loops as water of hydration.

All of the trials were carried out at an electrical current input of 50 amps (100 A/ft$^2$ current density). The concentration of the caustic product in the base loop was usually in the range of 110–130 gm/l, maintained by the metered addition of de-ionized water to the loop and the overflow of the product. Current efficiency (i.e., the equivalents of caustic produced per faraday of current output) was determined by measuring the output volume and the product concentration (via titration with standard HCl).

The production of amino acid hydrochloride was tested with a lysine feed. The lysine feed which was in the form of free base, had a pH of ~8.5–10. The lysine was metered into the acid loop, where it reacted with the HCl produced therein. The concentration of lysine in the feed solution was in the range of 100–500 gm/l and contained 10–25 ppm calcium and 20–80 ppm magnesium. Depending on the metering rate and concentration of the lysine feed, the pH of the product acid was in the range of 0.5 to 6.5, the lower figure representing approximately, the di-hydrochloride (lysine.(HCl)$_2$), and the higher pH of the hydrochloride salt (lysine.HCl). AHA-2 anions were used in the hydrochloride production.

Material balances around the acid loop showed excellent retention of the calcium and magnesium values within the loop. This was further confirmed because the base and salt loop products showed no net increases in the divalent metals. Consequently, a pretreatment of the amino acid feed to remove the calcium, magnesium values was not needed for the acid loop feed.

EXAMPLE 1

A long term trial on lysine hydrochloride production was carried out in a three compartment ED cell. For the first 313 hours of operation, the salt feed solution was treated with sodium hydroxide and carbonate and then was nanofiltered prior to feeding the salt loop of the cell under a conductivity control as described earlier. The cell operated at a temperature of 32–35° C. (90–95° F.). The nanofiltered feed had 0–6 ppm calcium and no detectable magnesium. A lysine solution was metered into the acid loop. The hydrochloride solution overflowed. The containment of the lysine solution within the acid loop was excellent. The material balance between the feed and the overflowed acid product showed the retention of lysine, calcium, and magnesium values within the acid loop.

The sodium hydroxide product from the base loop averaged ~117 gm/l, was water white, and showed no detectable lysine. This product caustic contained 100–500 ppm chloride. The current efficiency for caustic production averaged ~90%. The overall cell voltage was stable at 25–28 V. Allowing ~5V for the electrode rinse compartments, this translates to 2.5–2.9V per cell for the eight cell unit.

In the salt loop, the feed salt concentration was reduced by the transport and conversion of the salt values. The feed contained ~60 gm/l sodium, while the overflow had 12–35 gm/l sodium. The salt overflow was alkaline, containing 2–10 gm/l NaOH. This shows that the anion membrane has excellent retention for the acid values generated in the cell. The salt overflow was also water white, with its analysis showing no detectable level of lysine.

EXAMPLE 2

The second phase of the trial was continued for an additional 688 hours. In this phase, small amounts of a chelating agent (EDTA in the form of its potassium salt) was added to the salt feed solution either before or after nanofiltration, so that the salt solution fed to the cell had a certain amount of EDTA present. When the salt solution was prepared from rock salt, activated carbon (40 gm. of pellet carbon per 80 lb. of salt) was also added in the salt solution preparation step. The salt solution was nanofiltered as in Example 1 and fed to the cell under a conductivity control. The acid and base loops were operated as in Example 1. The cell operating temperature was generally in the range of 40–43° C. (100–115° F.).

During the 688 hours of operation, the sodium hydroxide product and the salt overflow continued to remain water white and showed no detectable level of lysine. The caustic strength and chloride level were similar to Example 1.

The salt feed solution contained 2–22 ppm calcium and no detectable magnesium. The higher calcium levels were in feeds where the EDTA had been added to the feed prior to nanofiltration. This addition, reduced the selectivity of the nanofilter for calcium retention. Nevertheless, a material balance around the salt loop showed that the calcium was effectively retained within the salt loop. (See my co-pending application Ser. No. 09/193,626, filed Nov. 11, 1998.) It appears that the cation and anion exchange membranes bounding the salt loop have an excellent retention for the calcium complex formed with the EDTA. Consequently, there was very little, if any, fouling of the cation membranes which is confirmed by a relatively steady cell voltage of ~25–28V. The stability of the cation membrane was further confirmed by the observation that the electrical cell current efficiency for caustic production was stable at ~90%.

At the conclusion of the test, the cell was opened and inspected. Both gaskets and the membranes were in excellent condition. The long term viability of the process for amino acid hydrochloride production is thereby established.

EXAMPLE 3

The ED cell was reassembled using recycled bipolar and anion membranes that were previously used during the above-described tests. A new set of SPS cation membranes were used. A new test was then carried out for 311 hours. The feed salt solution was prepared as before, but without the addition of a chelating agent and filtered through a cartridge filter. The solution was then nanofiltered, heated to ~70° C., and further pre-treated by passing it through an ion exchange column containing a C-467 chelating resin supplied by Rohm and Haas. The resin treatment reduced the calcium content of the feed stream to ~0.05 ppm. The acid, base, and salt loops were operated in the same manner as they were operated in Examples 1, 2.

The test results were also similar to those obtained in Examples 1, 2, the results including: product caustic quality, lysine retention in the acid loop, current efficiency for caustic production, and the cell voltage.

Figure 5:
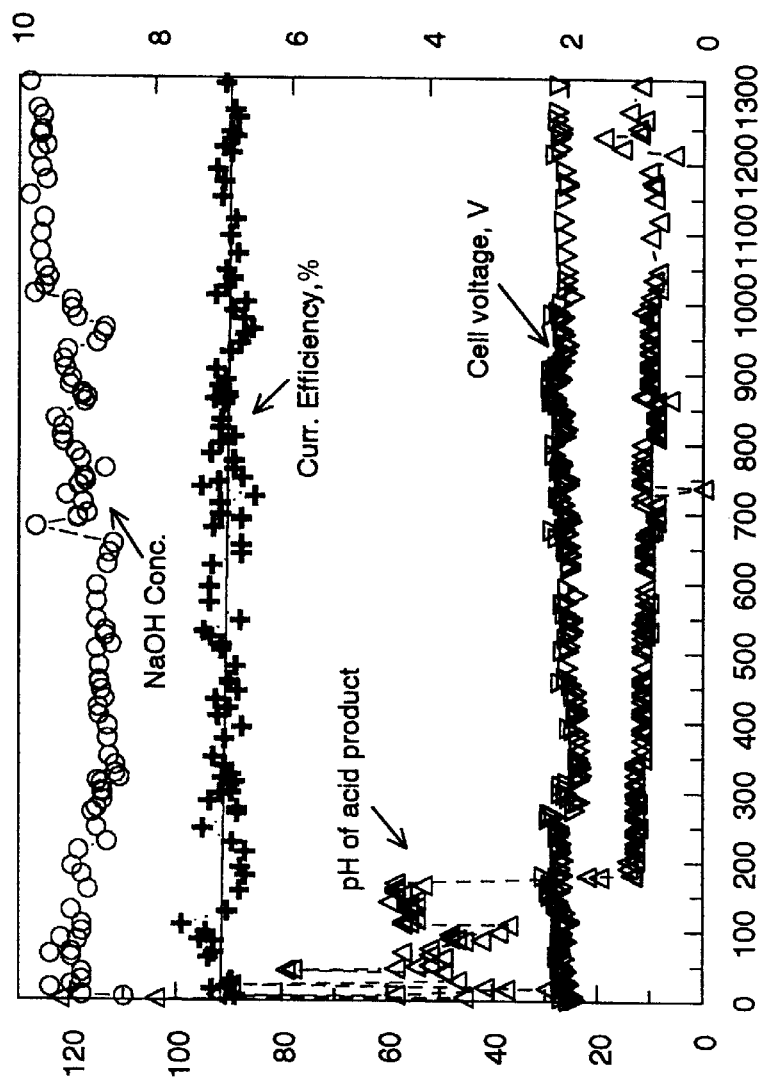
FIG. 5 is a graph which summarizes the test results described in the following examples.

FIG. 5 is a graph which shows a summary of the test results for Examples 1–3. The hours of operation shown along the horizontal axis are cumulative for the three examples. The first 313 hours being taken from Example 1, the next 688 hours from Example 2 and the final 311 hours from Example 3. It can be seen that the cell voltage and current efficiency were stable, indicating that the use of chelating resin pre-treatment (Example 3) or the use of chelating agent addition (Example 2) are substantially equally effective in mitigating the fouling of the cation membrane by calcium.

EXAMPLE 4

An 87 hour test for converting NaCl to NaOH and HCl was carried out in the pilot cell at the conclusion of the trial outlined in Example 2, by replacing the AHA-2 anion membranes with AAV anion membranes. The AAV anions are weak base membranes that have a higher efficiency for HCl generation. The test was carried out in the same manner as in Example 2, except that de-ionized water was added to the acid loop and a 5.5–6 wt % hydrochloric acid generated. The caustic soda product strength was ~115 gm/l.

The salt feed solution was pre-treated and nano-filtered as in Example 1. The chelating agent EDTA was added to the salt feed solution after the nanofiltration step. As with Example 2, the material balance showed good retention of the calcium within the salt loop. However, the current efficiency for the process was lower at ~80%. The salt loop was acidic due to the lower selectivity of the anion membrane vs. the cation membrane. The caustic soda product had an 1800–2800 ppm chloride contamination.

Figure 6:
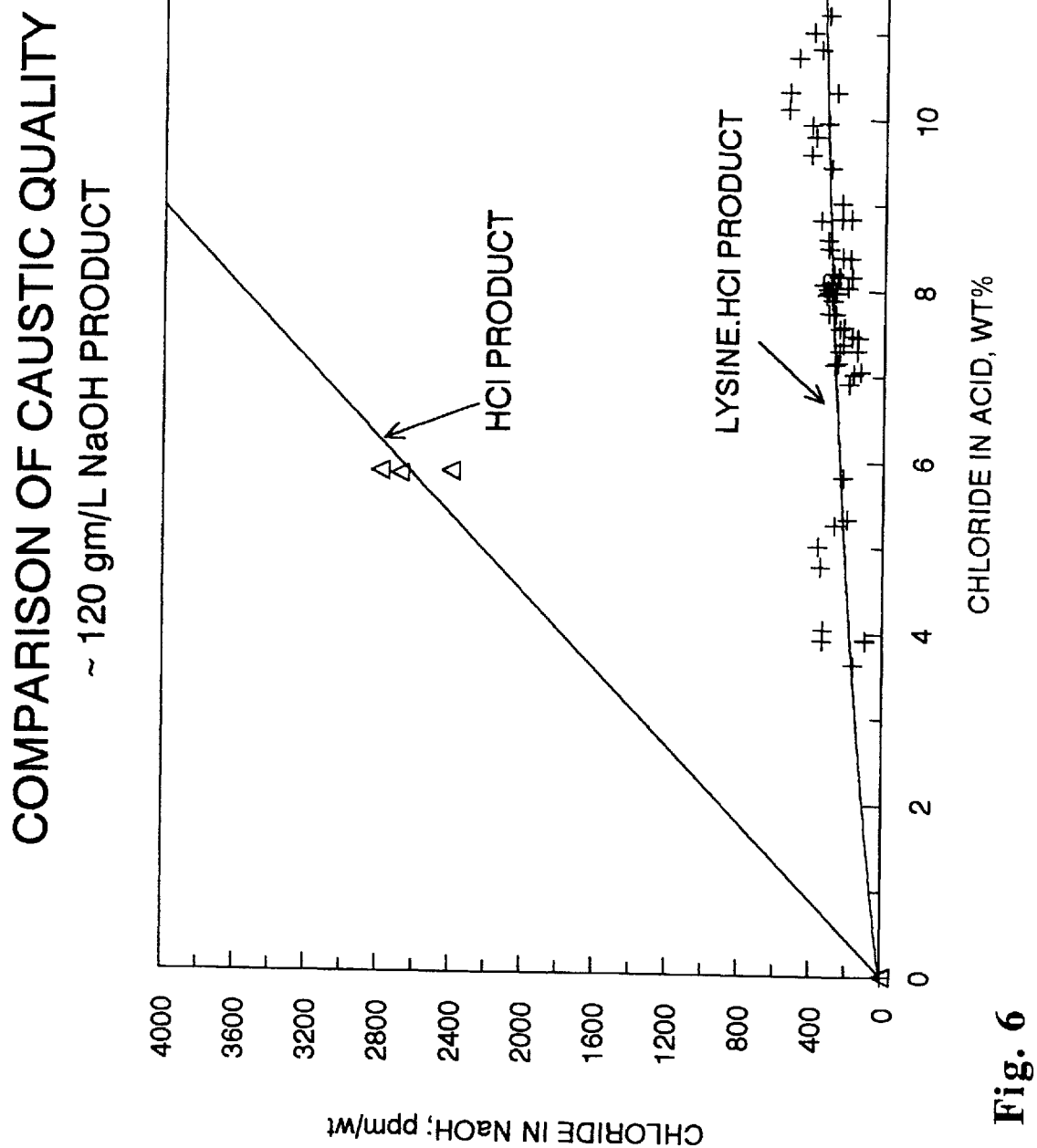
FIG. 6 is a graph which shows the chloride contamination of a caustic produced during the tests.

FIG. 6 shows the chloride contamination of the caustic product from the Examples 1–4 above. The top curve shows the results for HCl production (Example 4) and is in line with the 1–4% molar contamination reported in literature. The bottom curve shows the results for hydrochloride production (Examples 1–3). It can be seen that the quality of the caustic soda produced by the process of this invention is considerably superior, containing less than one tenth as much chloride as when HCl is the co-product.

EXAMPLE 5

The AHA-2 anion membranes from Example 1–3 were assembled with BP1 bipolar membranes and SPS cation membranes into an eight cell unit as shown in FIG. 3. A 150 hour test was carried out using the same procedure that is described in Example 3. The overall cell voltage was once again in the range of 25–28V for most of the test. The current efficiency was a bit lower ~80–84%, probably because of the differences in the selectivity of the SPS cation membranes used in this trial vs. the membranes used in Examples 1–3.

Table I shows a detailed analysis of one set of the salt overflow, caustic product, the lysine feed, and the lysine hydrochloride product streams. It can be seen that while lysine is the main component in the acid loop feed solution, there are also certain amounts of other amino acids. Importantly, all of the amino acids, including even the $C_2$ component glycine, are retained effectively within the acid loop so that they are undetectable in the base and salt loops.

Table I
LYSINE.HCl PRODUCTION PROCESS
Product analysis: Lysine.HCl from NaCl via ED
All values in ppm (w/w) except as noted.

|  | Lysine Feed | Lysine (HCl)$_x$ Product | Depleted Salt (Overflow) | NaOH Product |
|---|---|---|---|---|
| Aspartic Acid | ND | ND | ND | ND |
| Threonine | 110 | 52 | ND | ND |
| Serine | ND | ND | ND | ND |
| Glutamic Acid | 231 | 186 | ND | ND |
| Proline | ND | ND | ND | ND |
| Glycine | 107 | 127 | ND | ND |
| Alanine | 1809 | 1278 | ND | ND |
| Cystine | ND | ND | ND | ND |
| Valine | 4207 | 2795 | ND | ND |
| Methionine | 260 | 262 | ND | ND |
| Isoleucine | 376 | ND | ND | ND |
| Tyrosine | 1290 | 859 | ND | ND |
| Phenylanine | ND | ND | ND | ND |
| Lysine.HCl | 406 g/l | 290 (g/l) | ND | ND |
| Histidine | ND | ND | ND | ND |
| Arginine | 1802 | 1343 | ND | ND |

Typical Values for AQ Bipolars

| | | | | |
|---|---|---|---|---|
| Chloride | 1150 | 80300 | 32600 | 211 |
| Sodium | 161 | 1100 | 30800 | 63100 |
| Lysine.HCl | 372 g/l | 271 g/l | ND | ND |

Typical Values for BP1 Bipolars

| | | | | |
|---|---|---|---|---|
| Chloride | 1770 | 94300 | 53200 | 571 |
| Sodium | 226 | 310 | 37600 | 61900 |
| Lysine.HCl | 406 g/l | 290 g/l | ND | ND |

Table I also shows a comparison of the caustic and acid product quality using the AQ and BP1 bipolar membranes. When compared with the AQ bipolar membrane, the BP1 bipolar membrane appears to have a slightly lower sodium transport to the acid loop and a slightly higher chloride transport to the caustic loop. In general, both membranes generated a good quality caustic product.

Amino acid hydrochlorides can also be produced using potassium chloride as the feed salt. In this event, the co-product would be potassium hydroxide, KOH.

Figure 7:
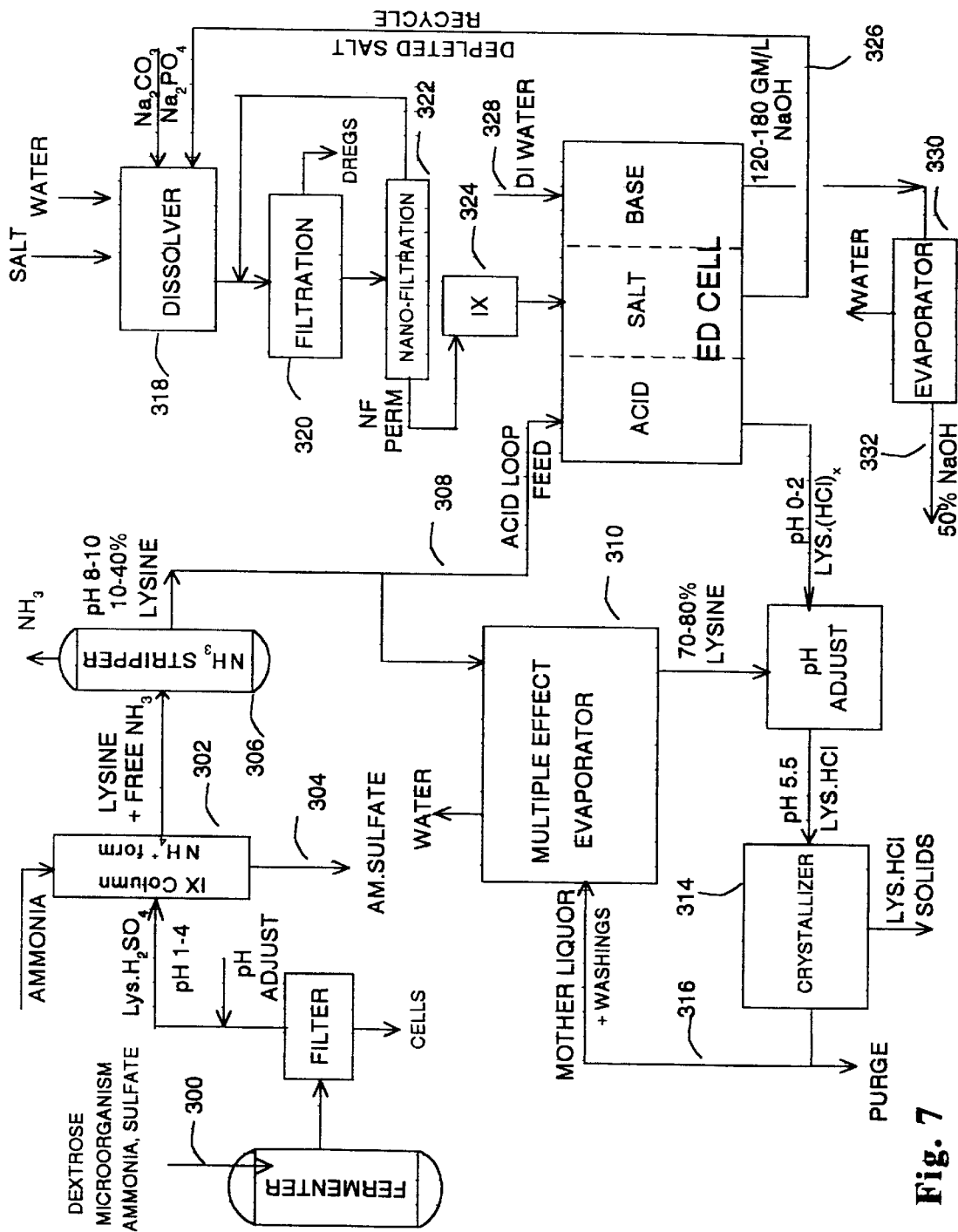
FIG. 7 is a block diagram showing a system using the invention to produce lysine.HCl.

FIG. 7 is a block diagram which can be studied to learn the process flow. It also shows the utility of this invention for the production of lysine.HCl. The lysine feed to the acid loop of the electrodialysis (ED) cell is obtained via a fermentation of dextrose (shown at 300 in the upper left of FIG. 7). The output from the fermenter is in the form of an impure sulfate salt (or chloride) indicated as lys.H$_2$SO$_4$ at a pH of 2–4). This solution is purified by passing it through an ion exchange column 302; with lysine being eluted from the column using ammonia/ammonium hydroxide in the initial step. (The lysine is selectively absorbed onto the resin, while the sulfate values are eluted at 304 as ammonium sulfate. The absorbed lysine is then eluted with an ammonia solution.) The resulting free lysine, along with any excess ammonia is then forwarded to an ammonia stripper 306. A portion of the lysine solution from the ammonia stripper, at a pH of 8–10, is then fed at 308 into the acid loop of the ED cell, while the balance of the solution is forwarded to a multiple effect evaporator 310.

In the ED cell, the lysine in the acid loop feed is converted into hydrochloride by reaction with the HCl generated therein. The acid loop product is typically lysine.(HCl)$_x$, where x is ~1.5 to 2. Its pH is in the range of 0–2. It is then forwarded to a pH adjustment at 312. Here, the low pH product is mixed with the concentrated lysine from the multiple effect evaporator 310 to obtain a 1:1 composition of the lysine.HCl salt, at a pH of ~5.5. The hydrochloride salt is then crystallized at 314 and the bulk of the mother liquor and washings are recycled at 316 to the multiple effect evaporator 310 for water removal. Optionally, the lysine HCl salt solution may be further purified to remove cations such as Na, K, etc., by passing through a cation exchange column (not shown) prior to the crystallization step.

The raw material for the ED cell is obtained by dissolving commercially purchased salt in a recycle salt solution along with make up water so as to obtain a nearly saturated solution. Since the recycle depleted salt solution is typically alkaline, further caustic addition may not be needed to raise the pH to the 9–10.5 range.

Sodium carbonate and/or sodium phosphate are added in order to promote the precipitation of calcium, magnesium and iron compounds. The resulting solution is filtered at 320 to remove the bulk of insoluble materials and then subjected to nanofiltration at 322. The nanofiltered feed is then passed through an ion exchange column 324 containing a chelating cation resin in order to further reduce the residual dissolved calcium content. Optionally a chelating agent such as EDTA may be added to the nanofiltered salt feed. The salt feed thus pretreated is then fed to the salt loop of the ED cell.

In the ED cell, a portion of the salt is converted to caustic and hydrochloric acid. The depleted salt solution overflows at 326 and is taken out of the salt loop and forwarded to the salt dissolution step.

The hydrochloric acid generated in the acid loop reacts with the lysine feed to yield the hydrochloride. At 328, de-ionized water is added to the base loop in order to pick up the caustic generated therein. Dilute caustic at a concentration of 100–200 gm/l overflows out of the base loop and is optionally concentrated to the 45–50 wt % range in an evaporator 330. The resulting solution is delivered at 332, ready for sale.

Those who are skilled in the art will readily perceive modifications of the inventive process. Therefore, the appended claims are to be construed to include all equivalent structures and processes which fall within the spirit and scope of the invention.

I claim:

1. A process for producing amino acid hydrochloride and an alkali in a three compartment electrodialysis cell containing bipolar, cation and anion membranes, said membranes being arranged to form acid, base, and salt compartments, the process comprising the steps of:

a. supplying a stream of salt solution to a salt compartment of an electrodialysis cell, a stream comprising water to a base compartment of said cell, and a liquid comprising an amino acid to an acid compartment of said cell;

b. applying a direct current driving force across said cell to produce a conversion of salt to an alkali solution in the base compartments and the amino acid to hydrochloride in the acid compartment; and c. withdrawing the acid and alkali solutions produced step b along with depleted salt solutions, the withdrawal being taken from the respective compartments.

2. The process of claim 1 wherein the salt stream of step a is selected from a group consisting of sodium chloride or potassium chloride, or lithium chloride and the corresponding alkali product is sodium hydroxide or potassium hydroxide or lithium hydroxide.

3. The process of claim 1 and a further step of purifying the salt stream before step a to reduce multivalent contaminants to a low level prior to an introduction of said salt stream into said salt compartment during step a.

4. The process of claim 1 and a further step of adding a chelating agent to the salt stream of step a prior to supplying it to said salt compartment.

5. The process of claim 1 and a further step of converting and concentrating the alkali solution to a concentration of 50–200 gm/l during step b.

6. The process of claim 5 and a further step of evaporating the alkali solution after step c for a further concentration thereof.

7. The process of claim 1 wherein the amino acid of step a is a molecule with at least three carbon atoms.

8. The process of claim 1 wherein the amino acid of step a is selected from a group consisting of arginine, lysine, hydroxylysine, histidine, and mixtures thereof.

9. The process of claim 1 wherein the amino acid of step a is lysine, and the acid withdrawn in step c is lysine hydrochloride, containing 1 to 2 equivalents of chloride per mole of lysine.

10. The process of claim 9 and a further step of concentrating the lysine in step a at a concentration of 100–500 gm/l.

11. The process of claim 9 wherein lysine is produced via fermentation before its submission to the electrodialysis cell in step a.

12. The process of claim 1 and the further steps of fortifying and purifying a depleted salt solution withdrawn in step c by adding fresh salt to said depleted salt solution, and recycling said fortified and purified salt solution back into said salt compartment of said electrodialysis cell.

13. a process for producing lysine hydrochloride, said process comprising the steps of:
   a. producing lysine salt solution by a fermentation of an organic substrate;
   b. obtaining a purified lysine solution by passing a filtered solution of step a through a cation exchange column and elution of the captured lysine using an ammoniacal base solution;
   c. dividing the purified solution of step b into two parts, with one part being converted by acidification to hydrochloride salt in a three compartment electrodialysis cell, using an alkali chloride salt feed and a direct current driving force; while the second part is concentrated in an evaporator;
   d. combining the two parts from step c using a pH adjustment to obtain a lysine hydrochloride solution with about a 1:1 ratio of lysine to hydrochloric; and
   e. crystallizing the hydrochloride salt from step d out of the solution.

14. The process of claim 13 wherein the lysine hydrochloride from step d is passed through a cation exchange column to remove contaminating cations prior the crystallization step e, said contaminating cations including at least one of sodium, potassium, calcium and magnesium.

15. The process of claim 13 wherein the salt used to provide the hydrochloride component is selected from a group consisting of sodium chloride, or potassium chloride, or lithium chloride.

* * * * *